Oct. 11, 1932.
G. H. DALRYMPLE
FREESIA
Filed Jan. 13, 1932
Plant Pat. 32
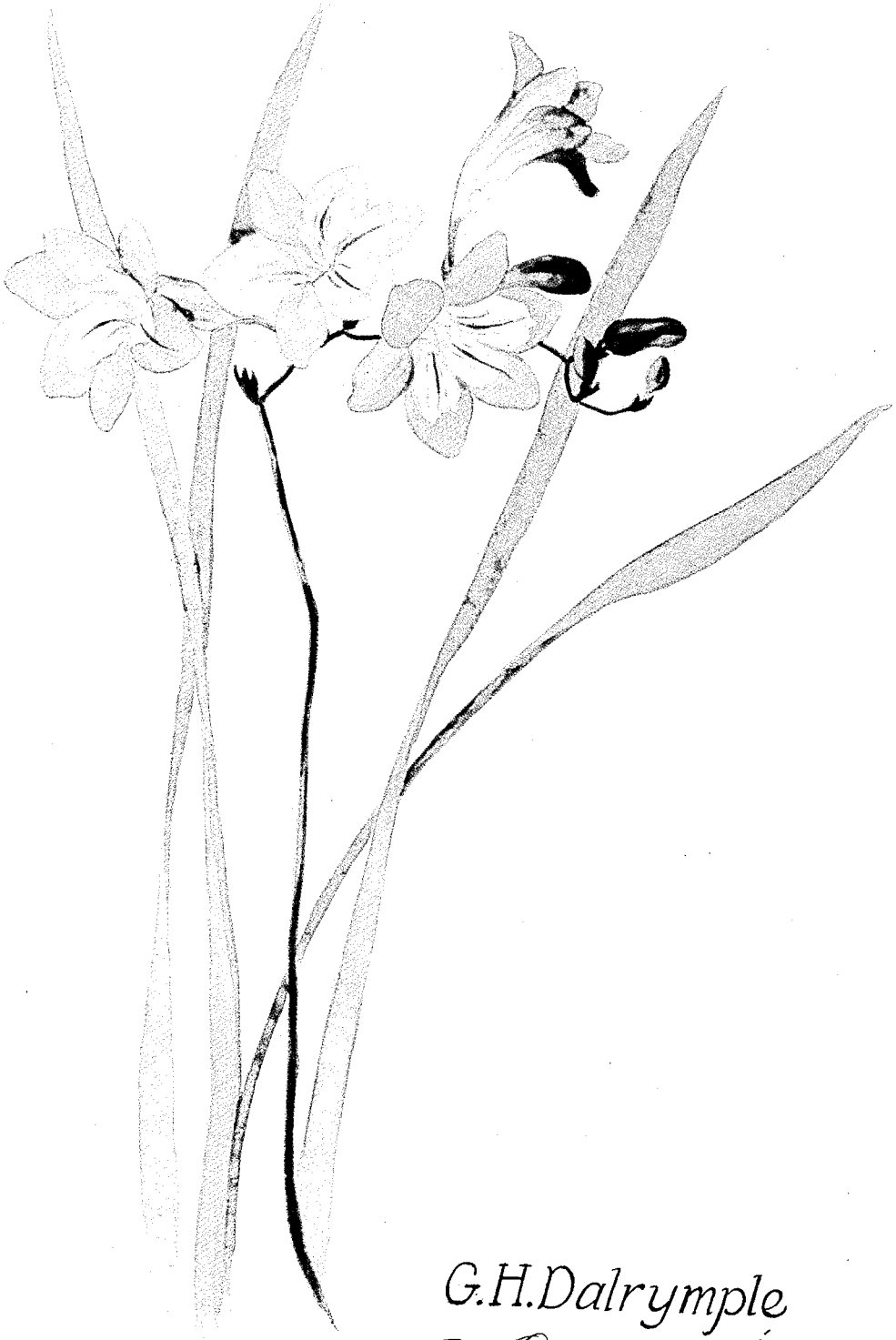
G.H.Dalrymple
By Orville M. Kile
PLANT PATENT AGENT Patented Oct. 11, 1932

Plant Pat. 32

UNITED STATES PATENT OFFICE

GERALD HEW DALRYMPLE, OF BARTLEY, NEAR SOUTHAMPTON, ENGLAND, ASSIGNOR TO C. J. VAN BOURGONDEIN, OF BABYLON, NEW YORK

FREESIA

Application filed January 13, 1932. Serial No. 586,435.

My invention relates to improvements in tinted or colored freesias. The object of my invention is to provide a freesia of the general type mentioned, having large blossoms, many flowers on a single spike a goodly number of which open at one time, having a pleasing lavender mauve color, petal lips or segments that stand out almost at right angles to the tube, stems sufficiently strong to hold the blossom spike upright, and having other desirable and useful characters.

My new freesia was produced first by selecting self-pollinated seedlings from the variety "La France", one of which was exceptional in quality and was named "Wistaria"; from "Wistaria" further new seedlings were produced and among these was discovered the original specimen of the new variety which is further described below. After reproducing this new variety for several years and testing it to make sure of the permanency of its superior qualities, I sold the entire stock of this variety in the fall of 1930 to Mr. C. J. Van Bourgondien, of Babylon, New York, who took this stock to his home in New York State and as late as August, 1931 still owned and possessed the entire stock.

The accompanying illustration shows in approximately natural size and colors a branch of my new freesia including four fully opened flowers, several buds, and an empty sepal cup from which the first-opened blossom has fallen. Two leaves are also shown.

The following is a detailed description of this new variety of freesia.

*Flowers.*—As many as ten to twelve flowers are borne on a single spike although the more usual number is eight or nine, borne upright along a somewhat irregularly jointed axis which is abruptly bent at right angles to the vertical main stem or peduncle. The perianth is funnel-shaped, long and gracefully slender, the six segments or lobes at the top of the perianth turning back when fully opened to a position almost at right angles with the tube, thus giving a wide expanse of color. The lobes are regular in formation, rounded at the ends. Four flowers of each spike are in bloom at a time and a fifth is in the form of a bud showing color but not yet opened. Flowers measure one and one-half to two inches across the top.

The dominant color tone may be popularly described as a lavender mauve. By reference to Ridgeway's Color Standard and Nomenclature, edition of 1912, the dominant color tone of the newly opened flowers is determined to be "light lavender-violet" to "light mauve" (Plate XXV). This is the color of the upper portions of the lobes, both inside and outside, except that some of the lobes show a deeper shade identified as "lavender-violet" to "mauve" (Plate XXV). Farther down the perianth much lighter shades are found, both inside and outside, and on three lobes of each flower the color at the throat becomes nearly white with touches of yellow. Still farther down the funnel distinctly yellow tones are found inside and faint shades of yellow are visible outside.

*Sepals.*—Two in number, are loose fitting and while they are long enough to completely cover the ovaries they do not extend as far up the sides of the funnel of the blossom as is usual in certain other large-flowered varieties. One sepal has a deep division, giving a two-toothed effect.

The plant grows 30 inches high, or more, under normal conditions, and has long slender leaves of a "light bice green" (Plate XVII).

The principal features which I believe distinguish my new variety from all other known varieties of freesias are:

First, relatively large size of plants and blossoms.

Second, distinctive "lavender-mauve" color with whitish throat.

Third, large number of flowers produced on each spike, with four flowers displayed at the same time.

Fourth, sepals shorter and less prominent than on certain other large-flowered varieties.

I claim:

The freesia as shown and described, characterized particularly by the "lavender-mauve" color and large size of its blossoms, the large number of blossoms per spike, four blossoms open at a time, and ample foliage of a light green color.

G. H. DALRYMPLE.